| United States Patent [19] | [11] Patent Number: 4,808,704 |
| Old et al. | [45] Date of Patent: * Feb. 28, 1989 |

[54] MONOCLONAL ANTIBODIES TO CELL SURFACE ANTIGENS OF HUMAN MALIGNANT MELANOMA

[75] Inventors: Lloyd J. Old, New York, N.Y.; Herbert F. Oettgen, New Canaan, Conn.; Hisami Ikeda, Asahikawa, Japan; Lucy T. C. Li, New York; Kenneth O. Lloyd, Bronx, both of N.Y.; Wolfgang G. Dippold, Mainz, Fed. Rep. of Germany

[73] Assignee: Sloan-Kettering Institute for Cancer Research, New York, N.Y.

[*] Notice: The portion of the term of this patent subsequent to Mar. 26, 2002 has been disclaimed.

[21] Appl. No.: 868,872

[22] Filed: May 22, 1986

Related U.S. Application Data

[63] Continuation of Ser. No. 307,060, Sep. 30, 1981, abandoned.

[51] Int. Cl.$^4$ .................... A61K 39/395; C12N 5/00; C12N 15/00; C12P 21/00
[52] U.S. Cl. .................... 530/387; 435/68; 435/172.2; 435/240.27; 935/194; 935/110
[58] Field of Search .................... 435/68, 172.2, 240, 435/948; 424/85, 88; 935/104, 110; 532/387

[56] References Cited

U.S. PATENT DOCUMENTS 4,507,391 3/1985 Pukel et al. .................... 935/110

OTHER PUBLICATIONS

Yeh et al., "Cell Surface Antigens of Human Melanoma Identified by Monoclonal Antibody", Proceedings of the National Academy of Sciences, vol. 76(6) (6–1979), pp. 2927–2931.

Woodbury et al., "Identification of a Cell Surface Protein, P97, in Human Melanomas and Certain Other Neoplasmas," Proceedings of the National Academy of Sciences 77(4) (4–1980), pp. 2183–2187.

Koprowski et al., "Study of Antibodies Against Human Melanoma Produced by Somatic Cell Hybrids," Proceedings of the National Academy of Sciences 75(7) (1978), pp. 3405–3409.

Suter et al., "Use of an Elisa for Screening of Hybridoma Antibodies Against Cell Surface Antigens," Journal of Immunological Methods, 39 (1980) pp. 407–411.

Imai et al., "Monoclonal Antibodies to Human Malanoma-Associated Antigens", Transplantation Proceedins, vol. XII, (3) (9–1980), pp. 380 –383.

Steplewski et al., "Monoclonal Antibodies to Human Tumor Antigens", Transplantation Proceedings, vol. XII (3) (9–1980), pp. 384–387.

Johnson et al., "Use of Monoclonal Antibodies to Characterize Melanoma Associated Antigens", Zeitschrift fuer Immunitaetsforschung Immunobiology, Stuttgart, 157(3) (1980), pp. 231–232.

Hellstrom et al., "Monoclonal Antibodies to Tumor-Associated Antigens in Human Melanoma", American Association for Cancer Research, Proceedings 21 (3–1980), p. 221, #889.

Brown et al., "Structural Characterization of Human Melanoma-Associated Antigen p97 with Monoclonal Antibodies", Journal of Immunology 127(2) (8–1981), pp. 539–546.

Primary Examiner—John E. Tarcza
Attorney, Agent, or Firm—John P. White

[57] ABSTRACT

Monoclonal antibody recognizing human melanoma cells, method of production and use.

7 Claims, No Drawings

MONOCLONAL ANTIBODIES TO CELL SURFACE ANTIGENS OF HUMAN MALIGNANT MELANOMA

This invention was made in part with government support under government grants CA 08748, CA 19765-03, CA 21445 and CB 74124 from the National Cancer Institute. Accordingly, the government has certain rights in this invention.

This application is a continuation of application Ser. No. 307,060, filed Sept. 30, 1981, now abandoned.

The invention described herein was made in the course of work under a grant or award from the Department of Health, Education and Welfare.

BACKGROUND

The present invention relates to the generation of monoclonal antibodies and their use in identifying or characterizing human malignant melanoma antigens. This is a useful diagnostic tool in the detection of human malignant melanoma as well as the study of the nature of human malignant melanoma. Immunofluorescent or enzymatic tagging agents can be bound to the highly specific antibodies provided by this invention, using normal procedures, as required for indexing methods. Cytotoxic agents can also be bound to the highly specific antibodies to produce so called "magic bullet" type therapeutic agents which selectively destroy the cells with which the specific antibody binds.

Other investigators have studied melanoma including Koprowski, et. al. Proc. Natl. Acad. Sci. USA 75, 3405–3409 (1978); Yeh, et al. (proc. Natl. Acad. Sci. USA 76, 2927–2931 (1979) and Woodbury et al. Proc. Natl. Acad. Sci. USA 77, 2183–2187 (1980). (The work of the present invention has also been published and is available in the same Journal i.e. Dippold et al. Proc. Nat'l. Acad. Sci. (1980) 77: 6614–6118 and is hereby incorporated by reference. Of these, the p97 melanoma surface antigen described by Woodbury et al may be related to the gp 95 antigen identified by 6 of the monoclonal antibodies of the invention.

BRIEF DESCRIPTION 18 mouse monoclonal antibodies derived from fusions with spleen cells of mice immunized with established melanoma cell lines identified 6 distinct antigenic systems: 2 antigenic systems being glycoproteins with molecular sizes of 95,000 and 150,000 daltons (gp95 and gp150); 2 antigenic systems being associated with heat-stable molecules having the characteristics of glycolipids ($O_5$ and $R_{24}$); and 2 antigenic systems ($M_{19}$) and $R_8$) being heat labile (molecular characterization has not been possible).

$O_5$ is a species antigen, being present on virtually every human cell type tested, gp95, gp150, $M_{19}$, and $R_8$ are found on a characteristic proportion of melanomas, astrocytomas, and epithelial cancers and on normal kidney cells. The antigen defined by the $R_{24}$ antibody has the most restricted distribution of all. Reactivity is found with melanomas and astrocytomas, whereas epithelial cell types, fibroblasts, and cells of hematopoietic origin lack $R_{24}$. Although occurrence of gp95, gp150, $M_{19}$ and $R_8$ distinguishes a small subset of melanomas not expressing these antigens, $R_{24}$ is found on all melanoma cells.

DESCRIPTION

Using the hybridoma technology (using the NS/1 mouse myeloma fusion cell line, ATCC #TIB 18) described by Köhler and Milstein, Nature (London) 256, 295–497 (1975), a series of monoclonal antibody producing hybridoma cell lines were produced and cultured to generate monoclonal antibodies.

Eighteen monoclonal antibodies detecting cell surface antigens of the immunizing melanoma cell line SK-MEL-28 on deposit with the ATCC as HTB72 were analyzed in this series. Antibodies reacting with HLA, Ia, or $\beta_2$m antigens were excluded during initial screening. The fine serological specificity of the 18 antibodies was tested on a panel of 41 established human cell lines (16 melanomas, 5 astrocytomas, 13 epithelial cancers, 6 B- and T-cell lines, and 1 fetal cell line) and on early cultures of fetal brain, adult kidney epithelium, skin fibroblasts, and melanocytes. In addition to cultured cells, we examined erythrocytes, peripheral blood leukocytes, and preparations of fetal liver, fetal brain, and adult brain. In most cases, serological analysis consisted of both direct tests and absorption tests. (Cultured melanocytes could not be obtained in sufficient number for absorption tests and preparations of adult human brain are not suitable for direct tests.)

Except for antibody $O_5$(see below), no reactions were observed with A, B, AB, or O human erythrocytes in direct hemagglutination tests and in absorption tests. Sheep erythrocytes, lyophilized guinea pig kidney, and purified preparations of human blood groups A, B, and O, Le$^a$ glycoproteins, and pneumococcal XIV polysaccharide were negative in absorption and inhibition tests. The possibility that fetal bovine serum components on cultured cells were being detected was ruled out by growing target cells in human serum for more than three passages before testing; no change in serological reactivity was observed.

These serological studies, in conjunction with immunoprecipitation analysis of radiolabeled cell extracts and antibody inhibition tests with solubilized antigen, indicate that the 18 monoclonal antibodies detect 6 antigenic systems. Two of the systems are glycoproteins with molecular sizes of 95,000 daltons (gp95) and 150,000 daltons (gp150), and two systems have characteristics of glycolipid antigens. The biochemical nature of the remaining two antigenic systems has not been determined.

gp95 Antigenic System. Six monoclonal antibodies [$I_{12(\gamma 2b)}$, $K_{5(\gamma 1)}$, $L_{1(\gamma 1)}$, $L_{10(\gamma 1)}$, $M_{17(\gamma 1)}$, and $R_{19(\gamma 1)}$] precipitated a 95,000-dalton component from labeled extracts of SK-MEL-28 showed inhibitory activity in the same molecular weight range. Because the antigen detected by these monoclonal antibodies bound to concanavalin A and could be labeled by surface $^{125}$I iodination and by metabolic incorporation of [$^{35}$S] methionine or [$^3$H] glucosamine, it was concluded that that the 95,000-dalton component is a cell surface glycoprotein (gp95). Both $I_{12}$ and $L_{10}$ precipitated gp95 components with the same isoelectric point, pI5.0 even though they showed differences in their serological reactivities. The gp95 determinants detected by these six monoclonal antibodies were heat labile.

The gp95 phenotype of our cell panel as analyzed with $I_{12}$ and $L_{10}$ is given in Table 1. With regard to the other gp95-detecting monoclonal antibodies, $K_5$ resembles $I_{12}$, whereas $L_1$, $M_{17}$ and $R_{19}$ resemble $L_{10}$ in their pattern of reactivity. Eleven melanoma cell lines showed strong reactivity (titer and strength of rosette formation) with the six monoclonal antibodies detecting gp95. SK-MEL-40 could specifically absorb the reactivity of these antibodies. SK-MEL-44 also demonstrated this direct-test-negative/absorption-test-positive phenotype with selected antibodies ($L_1$, $L_{10}$, $M_{17}$ and $R_{19}$). Three other melanoma lines (SK-MEL-29, -31, and -42) appeared to lack any gp95 expression as indicated by both direct tests and absorption tests. Comparable analysis of other human cell types showed that gp95 determinants can be demonstrated on a wide range of cell types, both normal and malignant. As in the case of melanoma cell lines, levels of gp95 ranged from easily detectable (e.g., T-24 and normal kidney epithelium) to detectable only by absorption tests (e.g., HT-29) to not demonstrable (e.g., AlAb and SK-OV-3).

Although the overall pattern of serological reactivity of the six different monoclonal antibodies detecting gp95 was similar, there were evident differences. For instance, the gp95 determinant detected by $L_{10}$ on several epithelial cancers in absorption tests was not detected by $I_{12}$. Further indication that the specificities of $I_{12}$ and $L_{10}$ were different comes from antibody inhibition tests with sodium deoxycholate/papain-solubilized preparations from SK-MEL-28. Fractionation of this material by gel filtration showed that inhibitory activity for $I_{12}$ was confined to one peak, whereas inhibitory activity for $L_{10}$ was found in two molecular weight ranges. These results suggest that at least two distinct determinants on the gp95 molecule are recognized by this series of monoclonal antibodies.

gp150 Antigenic System. Four monoclonal antibodies [$N_{9(\gamma 1)}$, $R_{23(\gamma 1)}$, $Q_{14(\gamma 1)}$, and $Q_{24(\gamma 1)}$] precipitated a 150,000-dalton component from labeled extracts of SK-MEL-28. A fifth antibody that did not have precipitating activity [$J_{11(\gamma 1)}$] is provisionally included in this group because of its related serological reactivity. Gel filtration chromatography of antigen solubilized by limited papain digestion of SK-MEL-28 showed inhibitory activity in the range 110,000–150,000-daltons. Surface labeling with $^{125}I$, metabolic labeling [$^{35}S$] methionine and [$^{3}H$] glucosamine, and concanavalin A binding indicate that the 150,000-dalton component is a cell surface glycoprotein (gp150). Both $N_9$ and $Q_{24}$ precipitated gp150 components with the same isoelectric point, pI 4.2, even though they showed differences in their serological reactivities. The gp150 determinants detected by these five monoclonal antibodies were heat labile.

The gp150 phenotype of our cell panel, as analyzed with $N_9$ and $Q_{24}$, is given in Table 2. $R_{23}$ and $Q_{14}$ resembled $N_9$ in their pattern of reactivity. The distribution of gp150 determinants is clearly distinguishable from that of gp95 (e.g. SK-MEL-29 and -42, two melanoma cell lines that are gp95-negative, are strongly gp150-positive; SK-MEL-79, which is gp150-negative, is strongly gp95-positive). gp150 determinants were found on a wide range of other cell types of normal and malignant origin. As with gp95, levels of gp150 on different cell types (even on those derived from the same cell lineage) varied from easily demonstrable in direct tests to demonstrable only by absorption to not detectable. Absorption analysis indicated that at least two distinguishable determinants were recognized on gp150 by this series of monoclonal antibodies. The gp150 determinant detected by $N_9$, $R_{23}$, and $Q_{14}$ appeared to be closely related or identical and could be distinguished from that detected by $Q_{24}$ on the basis of absorption tests with ME-180, SK-OV-3, and SK-LC-LL epithelial cancer lines.

$M_{19}$ and $R_8$ Antigenic systems. The reactivity of $M_{19(\gamma 1)}$ and $R_{8(\gamma 1)}$ in direct serological tests and absorption analysis (Table 3) defined two distinct antigenic systems unrelated to gp150, gp95, or the other surface antigens detected by our present battery of monoclonal antibodies. The antigenic determinants recognized by $M_{19}$ and $R_8$ were heat labile. In the case of $M_{19}$, gel filtration chromatography of antigen solubilized by limited papain digestion of SK-MEL-28 showed inhibitory activity for $M_{19}$ antibody in the 50,000–70,000 molecular weight range. No inhibitory activity of solubilized antigen was found with $R_8$ antibody. As yet, it has not been possible to immunoprecipitate antigen from radiolabeled extracts of SK-MEL-28 with either $M_{19}$ or $R_8$ antibodies.

$O_5$ Antigenic System. The determinant recognized by $O_{5(\gamma 1)}$ was present (in variable amounts) on every human cell type tested, including erythrocytes. The $O_5$ determinant was heat stable. No antigenic activity could be detected in soluble extracts either by antibody inhibition tests or by immunoprecipitation.

Antigens Defined by the $R_{24}$ Monoclonal Antibody Group. Four monoclonal antibodies [$K_{9(\gamma M)}$, $I_{24(\gamma M)}$, $C_{5(\gamma 3)}$, and $R_{24(\gamma 3)}$] defined antigens that were heat stable, and initial biochemical characterization indicated that glycolipid determinants were involved. They are grouped together because of their related serological reactivity, although it is not known whether they detect a single determinant or a family of determinants. The cellular distribution of antigens detected by the $R_{24}$ group (see Table 4 for $K_9$ and $R_{24}$) was more restricted than the distribution of gp95, gp150, $R_8$, $M_{19}$ and $O_5$ antigens. Melanomas and astrocytomas were the most reactive cell types, with other cells expressing little or no antigen. The virtual absence of these antigens on epithelial cancers was particularly striking. The antigen defined by the $R_{24}$ antibody was the most restricted of all, reactivity with cell lines being confined to melanomas and two of five astrocytomas.

The above hybridoma cell lines are maintained on deposit at Sloan-Kettering Institute for Cancer Research, 1275 York Avenue, New York, N.Y. 10022 under designations corresponding to the monoclonal antibodies produced by each hybridoma as follows:

LI 27 (M-1)
M 111 (M-4)
D 14 (M-8)
M 144 (M-10)
AL 1-27 (M-11)
LI 66 (M-12)
E 20 (M-13)
K 114 (M-16)
R 24 (M-18)
L235 (M-19)
L101 (M-20)
L230 (M-23)
L138 (M-24)
L368 (M-25)
A123 (M-26)
A124 (M-27)
B5 (M-28)

Upon granting of the patent, said hybridoma cell lines will be permanently available from the deposit with the American Type Culture Collection under ATCC designations corresponding to the above Sloan-Kettering designations as follows:

| Hybridoma Cell Line | Corresponding ATCC # |
|---|---|
| LI 27 (M-1) | HB 8437 |
| M 111 (M-4) | HB 8438 |
| D 14 (M-8) | HB 8439 |
| M 144 (M-10) | HB 8440 |
| AL 1-27 (M-11) | HB 8441 |
| LI 66 (M-12) | HB 8442 |
| E 20 (M-13) | HB 8443 |
| K 114 (M-16) | HB 8444 |
| R 24 (M-18) | HB 8445 |
| L235 (M-19) | HB 8446 |
| L101 (M-20) | HB 8447 |
| L230 (M-23) | HB 8448 |
| L138 (M-24) | HB 8449 |
| L368 (M-25) | HB 8450 |
| A123 (M-26) | HB 8451 |
| A124 (M-27) | HB 8452 |
| B5 (M-28) | HB 8453 |

TABLE 1
Characteristics of the gp95 antigenic system*

| Cells | Al $I_{12(\gamma 2b)}$ Titer × $10^{-3}$ | Abs | Ab $L_{10(\gamma 1)}$ Titer × $10^{-3}$ | Abs |
|---|---|---|---|---|
| *Melanomas* | | | | |
| SK-MEL-28,19,57,64,94 | 300 | + | 300 | + |
| SK-MEL-13,23,37,61,79,90 | 12 | + | 60 | + |
| SK-MEL-40 | — | + | 60 | + |
| SK-MEL-44 | — | — | — | + |
| SK-MEL-29,31,42 | — | — | — | — |
| *Astrocytomas* | | | | |
| AS,U138MG,U373MG | 12 | ± | 12 | + |
| AN,AJ | — | — | — | — |
| *Epithelial cancers* | | | | |
| Renal: | | | | |
| SK-RC-2 | 60 | | 300 | |
| SK-RC-9 | 12 | | 300 | + |
| SK-RC-6 | — | — | 2 | ± |
| SK-RC-7 | — | | — | |
| Breast: | | | | |
| BT-20,MCF-7 | — | — | — | + |
| AlAb | — | — | — | — |
| Bladder: T-24 | 60 | + | 60 | + |
| Ovarian: SK-OV-3 | — | — | — | — |
| Colon: HT-29 | — | + | — | + |
| Cervix: ME-180 | — | — | — | + |
| Lung: SK-LC-LL | — | — | — | — |
| Testicle: SK-GR-1 | — | + | — | + |
| *Lymphoblastoid cells* | | | | |
| T cell: | | | | |
| MOLT 4 | | — | | + |
| T-45 | | — | | — |
| EBV-B cell§ AH,BD,BT | — | — | — | + |
| *Normal cells* | | | | |
| Melanocytes | — | — | — | — |
| Fibroblasts | — | — | — | + |
| Kidney epithelium: 1,2 | 60 | | 300 | |
| Brain | | ± | | ± |
| Leukocytes | — | | — | + |
| Fetal fibroblasts | — | ± | — | ± |
| Fetal brain | — | — | — | — |
| Fetal liver | — | | — | |

*Antibody (Ab) subclass was determined on culture supernatants by double diffusion in agar with anti-Ig heavy chain specific reagents (Bionetics, Kensington, MD). Heat stability of antigenic determinants; labile (cells were exposed to 100° C. for 5 min and assayed for residual antigen activity in absorption tests). $M_r$ by immunoprecipitation: 95,000. $M_r$ by gel filtration; 70,000–100,000 (inhibitory activity was also found in the $M_r$ 35,000–55,000 region, see text).
—, No reaction in direct tests at a serum dilution of 1:50.
Abs, absorption tests. See ref. 3 for details. Serum (diluted according to end point) was absorbed with the indicated cell type and tested for residual activity for SK-MEL-28 target cells. +, Complete absorption; ±, partial absorption; —, no absorption.
§For direct tests with EBV-B cells, PA-MHA indicator cells wre used.

TABLE 2
Characteristics of the gp 150 antigenic system*

| Cells | Ab $N_{9(\gamma 1)}$ Titer × $10^{-3}$ | Abs | Ab $Q_{24(\gamma 1)}$ Titer × $10^{-3}$ | Abs |
|---|---|---|---|---|
| *Melanomas* | | | | |
| SK-MEL-28,13,19,23,29,37,40,42,57,64,90,94 | 1500 | + | 1500 | + |
| SK-MEL-61 | 60 | + | 60 | + |
| SK-MEL-44 | ± | + | — | — |
| SK-MEL-31,79 | — | — | — | — |
| *Astrocytomas* | | | | |
| AS,U138MG | 1500 | + | 1500 | + |
| U373MG | 300 | + | 60 | + |
| AN | 60 | + | — | + |
| AJ | — | — | — | — |
| *Epithelial cancers* | | | | |
| Renal: | | | | |
| SK-RC-6 | 300 | | 60 | |
| SK-RC-2,7 | — | | — | |
| SK-RC-9 | — | — | — | — |
| Breast: BT-20,MCF-7, | — | — | — | — |
| AlAb | | | | |
| Bladder: T-24 | 60 | + | 60 | + |
| Ovarian: SK-OV-3 | — | + | — | — |
| Colon: HT-29 | 60 | + | 60 | + |
| Cervix: ME-180 | — | + | — | — |
| Lung: SK-LC-LL | — | + | — | — |
| Testicle: SK-GR-1 | — | + | — | — |
| *Lymphoblastoid cells* | | | | |
| T cell: | | | | |
| MOLT 4 | | + | | — |
| T-45 | | — | | — |
| EBV-B cell§: | | | | |
| BD,BT | — | + | — | + |
| AH | — | + | — | — |
| *Normal cells* | | | | |
| Melanocytes | 1 | | 1 | |
| Fibroblasts | 2 | + | 0.5 | + |
| Kidney epithelium: 1,2 | 1500 | | 1500 | |
| Brain | | + | | ± |
| Leukocytes | — | | — | |
| Fetal fibroblasts | — | + | — | + |
| Fetal brain | 300 | + | 60 | + |
| Fetal liver | | + | | + |

*Methods, layout, and footnotes as in Table 1. Heat stability; labile. $M_r$ by immunoprecipitation: 150,000. $M_r$ by gel filtration 110,000–150,000.

TABLE 3

Characteristics of the $M_{19}$ and $R_8$ antigenic systems*

| | Serological tests Ab $M_{19(\gamma 1)}$ | | | Serological tests Ab $R_{8(\gamma 1)}$ | |
|---|---|---|---|---|---|
| Cells | Titer $\times 10^{-3}$ | Abs | Cells | Titer $\times 10^{-3}$ | Abs |
| *Melanomas* | | | | | |
| SK-MEL-28,64 | 1500 | + | SK-MEL-19,28, 42,90 | 1500 | + |
| SK-MEL-23,29,37 | 60 | + | SK-MEL-13,64 | 60 | + |
| SK-MEL-44,57,61, 90,94 | 12 | + | SK-MEL-23,57,79 | 12 | + |
| SK-MEL-31,79 | — | + | SK-MEL-29,37,40 | 0.5 | ± |
| SK-MEL-13,19,40,42 | — | — | SK-MEL-44,94 | — | — |
| | | | SK-MEL-44,94 | — | — |
| *Astrocytomas* | | | | | |
| AS,U138MG, U373MG | 60 | + | AS,U138MG | 2 | + |
| AN,AJ | — | + | AJ,AN,U373MG | — | — |
| *Epithelial cancers* | | | | | |
| Renal: SK-RC-6,9 | 60 | + | Renal: SK-RC-2,6, 7,9 | 60 | + |
| SK-RC-2 | — | — | | | |
| Breast: AlAb, BT-20,MCF-7 | — | — | Breast: AlAb, BT-20,MCF-7 | — | — |
| Bladder: T-24 | — | — | Bladder: T-24 | 60 | + |
| Ovarian: SK-OV-3 | 12 | + | Ovarian: SK-OV-3 | — | — |
| Colon: HT-29 | — | — | Colon: HT-29 | — | — |
| Cervix: ME-180 | — | — | Cervix: ME-180 | — | — |
| Lung: SK-LC-LL | — | — | Lung: SK-LC-LL | — | — |
| Testicle: SK-GR-1 | — | — | Testicle: SK-GR-1 | — | — |
| *Lymphoblastoid cells* | | | | | |
| T-cell: MOLT 4, T-45 | — | | T-cell: MOLT 4, T-45 | — | |
| EBV-B cell§: | | | EBV-B cell§: | | |
| BD,BT | — | + | BD,BT | — | — |
| AH | — | — | AH | — | — |
| *Normal cells* | | | | | |
| Melanocytes | 1 | | Melanocytes | 0.1 | |
| Fibroblasts | 12 | + | Fibroblasts | — | — |
| Kidney epithelium: 1,2 | 12 | | Kidney epithelium: 1,2 | 0.5 | |
| Brain | — | — | Brain | | + |
| Leukocytes | | + | Leukocytes | | + |
| Fetal fibroblasts | 2 | + | Fetal fibroblasts | — | ± |
| Fetal brain | — | — | Fetal brain | — | — |
| Fetal liver | | — | Fetal liver | — | — |

*Methods, layout, and footnotes as in Table 1. Heat stability: labile. $M_r$ of $M_{19}$ by gel filtration: 50,000–70,000.

TABLE 4

Characteristics of the $R_{24}$ antigenic system*

| | Serological tests | | | |
|---|---|---|---|---|
| | Ab $K_{9(IgM)}$ | | Ab $R_{24(\gamma 3)}$ | |
| Cells | Titer $\times 10^{-3}$ | Abs | Titer $\times 10^{-3}$ | Abs |
| *Melanomas* | | | | |
| SK-MEL-28,19,29 42,57,64,94 | 25 | + | 25 | + |
| SK-MEL-13,37,40,90 | 2 | + | 25 | + |
| SK-MEL-23,44,79 | 1 | + | 5 | + |
| SK-MEL-31,61 | — | + | 1 | + |
| *Astrocytomas* | | | | |
| AJ | 5 | + | 5 | ± |
| AN | — | + | — | + |
| AS,U138MG,U373MG | — | — | — | — |
| *Epithelial cancers* | | | | |
| Renal: | — | — | | |
| SK-RC-7 | | | | |
| SK-RC-2,6,9 | — | — | — | — |
| Breast: BT-20, MCF-7, AlAb | — | — | — | — |
| Bladder: T-24 | — | — | — | — |
| Ovarian: SK-OV-3 | — | — | — | — |
| Colon: HT-29 | — | — | — | — |
| Cervix: ME-180 | — | — | — | — |
| Lung: SK-LC-LL | — | — | — | — |
| Testicle: SK-GR-1 | — | — | — | — |
| *Lymphoblastoid cells* | | | | |
| T-cells: | | | | |
| MOLT 4 | | ± | | — |
| T-45 | — | | | |
| NALL | — | — | — | — |
| EBV-B cell§: AH,BD,BT | — | — | — | — |
| *Normal cells* | | | | |
| Melanocytes | — | | 0.1 | |
| Fibroblasts | — | ± | — | — |
| Kidney epithelium: 1,2 | — | — | | |
| Brain | | + | | ± |
| Leukocytes | | + | | — |
| Fetal fibroblasts | — | ± | | |
| Fetal brain | | + | | — |
| Fetal liver | | + | | — |

*Methods, layout, and footnotes as in Table 1. Heat stability; stable.

What is claimed is:

1. A monoclonal antibody panel capable of determining the presence of human malignant melanoma comprising at least one monoclonal antibody immunologically reactive with melanoma gp150 antigen and selected from the group consisting of $J_{11}$, $N_9$, $R_{23}$, $Q_{14}$ and $Q_{24}$ and at least one monoclonal antibody immunologically reactive with melanoma gp95 antigen and selected from the group consisting of $M_{17}$, $L_1$, $L_{10}$, $R_{19}$, $I_{12}$ and $K_5$.

2. A monoclonal antibody selected from the group consisting of $K_9$, $I_{24}$, $C_5$ and $R_{24}$ (ATCC No. HB8445).

3. The monoclonal antibody of claim 2 designated $R_{24}$ (ATCC No. HB8445).

4. A monoclonal antibody panel capable of determining the presence of human malignant melanoma comprising at least two monoclonal antibodies which are immunologically reactive with glycolipid melanoma antigen and are selected from the group consisting of $R_{24}$, $K_9$, $C_5$ and $I_{24}$.

5. A monoclonal antibody kit for melanoma diagnosis wherein the monoclonal antibodies have reactivity to glycoprotein and glycolipid melanoma antigens comprising at least one monoclonal antibody capable of immunological reaction with melanoma glycoprotein antigen gp95 selected from a group consisting of $M_{17}$, $L_1$, $L_{10}$, $R_{19}$, $I_{12}$ and $K_5$ or melanoma glycoprotein antigen gp150 selected from the group consisting of $J_{11}$, $N_9$, $R_{23}$, $Q_{14}$ and $Q_{24}$, and at least one monoclonal antibody capable of immunological reaction with melanoma glycolipid antigen.

6. Monoclonal antibody kit of claim 5 wherein the glycolipid reactive monoclonal antibodies are selected from the group consisting of $R_{24}$, $C_5$, $K_9$ and $I_{24}$.

7. A hybridoma cell line selected from the group of hybridoma producing monoclonal antibodies $R_{24}$ (ATCC No. HB8445), $C_5$, $K_9$ and $I_{24}$.

* * * * *